United States Patent
Bombardelli et al.

(10) Patent No.: US 7,993,683 B2
(45) Date of Patent: Aug. 9, 2011

(54) COMPOSITIONS FOR THE TREATMENT OF CHRONIC DEGENERATIVE INFLAMMATORY CONDITIONS

(75) Inventors: Ezio Bombardelli, Groppello Cairoli (IT); Paolo Morazzoni, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/376,452

(22) PCT Filed: Jul. 27, 2007

(86) PCT No.: PCT/EP2007/006666
§ 371 (c)(1),
(2), (4) Date: Nov. 9, 2009

(87) PCT Pub. No.: WO2008/017390
PCT Pub. Date: Feb. 14, 2008

(65) Prior Publication Data
US 2010/0047339 A1    Feb. 25, 2010

(30) Foreign Application Priority Data
Aug. 8, 2006 (EP) .................... 06016518

(51) Int. Cl.
*A61K 36/00* (2006.01)
*A61K 31/7012* (2006.01)

(52) U.S. Cl. ........................................ 424/725
(58) Field of Classification Search .................. None
See application file for complete search history.

(56) References Cited

FOREIGN PATENT DOCUMENTS
WO    2005002611 A     1/2005
WO    WO 2005/002611 A1 *  1/2005
WO    2005074953 A     8/2005

OTHER PUBLICATIONS

Madav et al, Anti-inflammatory activity of andrographolide, Fitoterapia, (1996) vol. 67, No. 5, pp. 452-458.*
"ICN Pharma Extends NYAL Range with Herbs", Nutraceuticals International, Marketletter, London, GB (Jan. 6, 2003).
Databse Prompt [Online] "Get Well Original Cold & Flu Formula—Vegicaps", Database Accession No. 1999:757722.

* cited by examiner

*Primary Examiner* — Qiuwen Mi
(74) *Attorney, Agent, or Firm* — Porzio, Bromberg & Newman, P.C.

(57) ABSTRACT

Compositions comprising:
saligenin or derivatives thereof or *Salix* ssp extracts containing from 10 to 50% of saligenin;
substantially pure andrographolide or andrographolide enriched *Andrographis paniculata* extract containing from 5 to 30% of andrographolide;
optionally N-acetyl-glucosamine and/or
glucuronic acid or glucuronolactone.

6 Claims, No Drawings

COMPOSITIONS FOR THE TREATMENT OF CHRONIC DEGENERATIVE INFLAMMATORY CONDITIONS

CROSS REFERENCE TO RELATED APPLICATION

This is a National Stage of International Application PCT/EP2007/006666, filed 27 Jul. 2007, which claims the benefit of Application No. 06016518.0, filed in Europe on 8 Aug. 2006, the disclosures of which Applications are incorporated by reference herein.

FIELD OF THE INVENTION

The present invention relates to formulations comprising combinations of analgesic/anti-inflammatory, immunomodulating and optionally cartilage-reconstructing agents for the treatment of degenerative inflammatory conditions such as rheumatoid arthritis and more generally, arthritis conditions.

The combination of these agents, acting through different mechanisms of actions, reduces pain and prevents the progression of joint injuries.

TECHNOLOGICAL BACKGROUND

Rheumatoid arthritis is a chronic degenerative disease which affects a large portion of elderly, causing serious problems to patients. The pathogenesis of rheumatoid arthritis and arthritis conditions is due at first to the immune system, and subsequently to inflammatory conditions which erode the intra-articular surfaces causing deforming damages which are irreversible and painful.

Bark and branches extracts of different species of *Salix* have been used for unmemorable time for the treatment of articular rheumatic forms and gout. *Salix* extracts were, however, substantially abandoned at the end of the 19th century, when acetylsalicylic acid was synthesized by acetylation of salicylic acid, obtained by oxidation of the compounds present in *Salix*. However, acetylsalicylic acid and *Salix* extracts have substantial differences in terms of mechanisms of actions and activity on bone joints. The extracts act on the enzyme COX 2, while acetylsalicylic acid mainly acts on COX 1, which involves the well-known side effects on the gastrointestinal tract and blood coagulation, which severely restrict its prolonged use which is conversely necessary in the case of such chronic-degenerative pathologies as arthrosis and rheumatoid arthritis. As an example a saligenin enriched *Salix* extract is prepared according to the patent application MI2005A001349 which is herein incorporated by reference.

*Andrographis paniculata* has been reported to have multiple pharmacological activities. These involve the stimulation of the immune system and the reduction of inflammation. It is well known that *A. paniculata* extract or its main components andrographolide inhibits the synthesis of pro-inflammatory cytokines. The addition of andrographolide to an endohelid cell culture together with tumour necrosis factor (TNF) effected a concentration depended reduction of the TNF-induced enhancement of endothelial monocyte adesion, which is part of the inflammatory process.

The primary active ingredient in *Andrographis paniculata* extract is andrographolide, a bitter diterpenoid lactone. The extract also contains other diterpenoid lactones, diterpene glucosides, diterpene dimers and flavonoids.

An extract for use in this invention can be prepared by immersing the aerial part of *Andrographis paniculata* in one or more suitable solvents such as ethanol, methanol and acetone; separating the liquid from the solid residues and concentrating the liquid. The extract thus obtained may be further processed. For example impurities can be removed the ratio of the component may be varied by known methods.

DISCLOSURE OF THE INVENTION

The present invention relates to compositions comprising a combination of active principles capable of inducing particularly significant therapeutic effects, without important side effects even after prolonged treatments.

The pharmaceutical formulations of the invention comprise:
  pure saligenin or derivatives thereof or *Salix* ssp extracts containing from 10 to 50% of saligenin;
  substantially pure andrographolide or andrographolide enriched *Andrographis paniculata* extract containing from 5 to 30% of andrographolide;
  and optionally N-acetyl-glucosamine and/or
  glucuronic acid or glucuronolactone.

The formulations of the invention preferably comprise:
  *Salix* ssp. extract containing 25% by weight of saligenin;
  *Andrographis paniculate* extract containing 15% by weight of Andrographolide and optionally N-acetyl-glucosamine and/or glucuronic acid or glucuronolactone.

The *Salix* extract and the *Andrographis paniculata* extract are preferably present in the formulations 2:1 weight ratios, respectively.

The formulations will contain typically 40 to 500 mg of *Salix* extract, 20 to 250 mg of *Andrographis paniculata* extract, and optionally 10 to 500 mg each of glucosamine and glucuronic acid or glucuronolactone.

The formulations will be in the form of soft- or hard-gelatin capsules, tablets or other forms suitable for the oral administration. Capsules containing *Enothera biennis* oil as a carrier are preferred.

N-Acetyl-glucosamine, glucuronic acid or glucuronolactone, which can be considered the building blocks of the connective tissue, complete the therapeutic profile of the formulations of the invention, as they promote the re-synthesis of proteoglycans in the joints, which is an important restoration process that, together with the aforementioned factors, can contribute to a symptomatic improvement.

The compositions of the invention can be administered for prolonged times, in one or repeated daily administrations, until recovery or relief from the symptoms.

The following examples further illustrate the invention.

Example I

Preparation of *Andrographis paniculata* Extract 1000 grams of *Andrographis paniculata* aerial part (biomass) are covered with 3.2 liters of 70% ethanol at 65° for 3 hours in a static percolator. Then the percolate is recovered and the biomass is extracted 5 times again under the same conditions, but using 2.6 liters of solvent per extraction, so obtain approximately 15.2 liters of percolate. The combined percolates are filtered and concentrated by a rotary evaporator at 60° under reduced pressure. The extract is dried at 60° under reduced pressure for one night. This extract has a total dry residue of 90.9 g, the yield vs starting material being 10.1 w/w. The Andrographolide HPLC content is 22.38%.

Example II

Preparation of Cellulose Capsules

Each capsule contains:

| | |
|---|---|
| *Salix rubra* extract (25% in saligenin) | 200 mg |
| *Andrographis paniculata* extract containing 15% of andrographolide | 100 mg |
| N-Acetyl-glucosamine | 100 mg |
| Glucuronolactone | 100 mg |
| *Enothera biennis* oil | q.s. to 700 mg |

The formulation of the Example I, when administered to patients suffering from rheumatoid arthritis conditions, showed consistent clinical results in terms of pain reduction, better mobility of the affected limbs, biopsic examinations of the joints and sense of well-being.

Example III

Preparation of Capsules

Each capsule contains:

| | |
|---|---|
| *Salix* extract (25% in saligenin) | 200 mg |
| *Andrographis paniculata* extract (containing 15% of Andrographolide) | 100 mg |
| Diacerhein | 100 mg |
| N-Acetyl-glucosamine | 100 mg |
| Glucuronolactone | 100 mg |
| *Enothera biennis* oil | q.s. to 700 mg |

The formulation of the Example I, when administered to patients suffering from rheumatoid arthtritis or arthritis conditions, showed consistent clinical results in term of pain reduction, better mobility of the affected limbs, biopsic examinations of the joints and sense of well-being.

The invention claimed is:

1. A composition comprising:
   200 to 500 mg of saligenin or *Salix* ssp extracts containing from 25% to 50% by weight of saligenin;
   100 to 250 mg of andrographolide or andrographolide enriched *Andrographis paniculata* extract containing from 15% to 30% by weight of andrographolide; and
   10 to 500 mg each of N-acetyl-glucosamine and/or glucuronic acid or glucuronolactone.

2. The composition according to claim 1 comprising:
   *Salix* ssp, extract containing 25% by weight of saligenin; and
   *Andrographis paniculate* extract containing 15% by weight of Andrographolide.

3. The composition according to claim 2 wherein the weight ratio of the *Salix* extract to the *Andrographis paniculata* extract is 2:1.

4. The composition according to claim 1 in form of soft- or hard-gelatin capsules, tablets or other forms suitable for oral administration.

5. The composition according to claim 4 in form of capsules containing *Enothera biennis* oil as a carrier.

6. A method for treating rheumatoid arthritis which comprises administering a therapeutically effective amount of a composition according to claim 1 to a subject in need thereof.

* * * * *